United States Patent [19]
Gao et al.

[11] Patent Number: 5,766,549
[45] Date of Patent: Jun. 16, 1998

[54] APPARATUS FOR DRYING BLOOD SMEAR SLIDES

[75] Inventors: Daniel Dashui Gao, Miami, Fla.; Marshall D. Graham, Nicholasville, Ky.; Manuel Calvo, Miami, Fla.

[73] Assignee: Coulter International Corp., Miami, Fla.

[21] Appl. No.: 557,228

[22] Filed: Nov. 14, 1995

[51] Int. Cl.⁶ ..................................................... G01N 21/00
[52] U.S. Cl. ........................... 422/65; 422/67; 118/100
[58] Field of Search ................................. 422/63, 65, 64, 422/67, 68.1; 436/47, 49; 118/100, 120, 506, 238

[56] References Cited

U.S. PATENT DOCUMENTS

| | | | |
|---|---|---|---|
| 4,061,108 | 12/1977 | Levine et al. | 118/100 |
| 4,096,824 | 6/1978 | Levine et al. | 118/100 |
| 4,319,542 | 3/1982 | Ojima et al. | 118/120 |
| 5,075,079 | 12/1991 | Kerr et al. | 422/64 |
| 5,209,903 | 5/1993 | Kanamori et al. | 422/65 |
| 5,356,595 | 10/1994 | Kanamori et al. | 422/65 |

*Primary Examiner*—Harold Y. Pyon
*Attorney, Agent, or Firm*—Warren W. Kurz

[57] ABSTRACT

Apparatus for drying a succession of microscope slides having wet blood specimen smears on a first major surface, including a belt transport for moving slides along a longitudinal drying path with their wet surfaces facing in a common direction and means for directing low velocity, heated air flows toward the non-smeared, major slide surfaces. Air flow proximate the slides preferably is about 15° C. above ambient and at a velocity of about 10 to 30 feet per minute for a drying period of about 75 to 135 seconds, per slide.

6 Claims, 5 Drawing Sheets

APPARATUS FOR DRYING BLOOD SMEAR SLIDES

CROSS-REFERENCE TO RELATED APPLICATION

Reference is made to the concurrently filed, commonly assigned U.S. application Ser. No. 08/557,226, entitled "Improved Apparatus and Method for Automated Production of Blood Smear Slides."

BACKGROUND OF THE INVENTION

1. Field of Invention

The present invention relates to improvements in apparatus for automatically producing blood smears on glass microscope slides. More particularly, it relates to an improved method and apparatus for automatically drying blood smears upon such slides.

2. Discussion of the Prior Art

Blood is often analyzed microscopically for various purposes, including determining the number of blood cells of different types and studying different cell morphologies. In order to improve the uniformity and the efficiency of such analyses, different devices have been designed to automate the process of smearing a blood drop on a glass microscope slide. The automated slide makers disclosed in U.S. Pat. Nos. 4,061,108 and 4,906,824 are illustrative of prior art devices in which the movement of a skive blade is controlled to smear a blood drop across a slide.

Upon spreading a blood drop across a planar surface of a glass microscope slide, it is common to dry the resulting blood smear prior to examining it under a microscope or, alternatively, prior to staining it for subsequent examination. Typically, the blood smear is simply allowed to dry under ambient conditions, the drying time being of the order of between 1 and 5 minutes, depending on ambient temperature and humidity. When an automated slide maker is used to produce a plurality of slides in a rapid sequence, it will be appreciated that the drying time must be the same for all conditions, and preferably as short as possible.

Like any other "wet" item, a wet blood smear can be dried more quickly when subjected to increased heat and air circulation. In U.S. Pat. No. 5,209,903, for example, a fan is used to direct air onto a wet blood smear to effect drying thereof. While such a direct approach is certainly effective to accelerate the drying of a blood smear, we have observed that this approach results in dramatic changes in cell morphology, i.e., the shape and appearance of many of the blood cells change when directly subjected to a heated air stream. More specifically, we have observed severe distortions in the appearances of neutrophils and lymphocytes which have been heated directly with an air stream, such distortions causing these cells to appear "box-like" and/or crenated in shape. This distortion makes it more difficult to identify and analyze these cells. Thus, we have found that there are substantial difficulties in providing a drying system that will automatically dry blood smears on glass slides within a reasonably small heating space, at a relatively rapid and uniform rate (sufficiently rapid to keep pace with the slide production capacity of an automated slidemaker apparatus), and without harmfully disturbing the respective morphologies of the blood cells.

SUMMARY OF THE INVENTION

One significant purpose of the present invention is to solve problems such as described above and provide, for an automated blood smear slide maker, an improved apparatus and method that enable the drying of slides at usefully high throughput rates, and minimize the distortion of cell morphologies. One important advantage of the present invention is that it minimizes the space and power requirements of a blood smear dryer in an automated slide-making apparatus. Another important advantage of the present invention is that it provides high quality, dried blood smears that accurately represent specimen blood cell morphologies. Another advantage of the present invention is that it facilitates the orderly input and output of slides to a slide-drying apparatus.

In one aspect, the present invention constitutes a dryer apparatus for drying a succession of blood smears on microscope slides having a wet blood specimen on a first major surface. The dryer apparatus comprises means for feeding the slides along a drying path with their wet surfaces facing in a common direction and means for directing low velocity, heated air flows generally toward the major slide surfaces that are opposite the wet slide surfaces, during their passage along the drying path.

In another aspect the present invention constitutes a method for automatically drying a succession of blood smear slides wherein the slides are transported seriatim along a heating path and heated air is directed toward their non-wetted major surfaces for a predetermined time period, at a predetermined flow rate and at a predetermined temperature.

The invention and its various advantages will be better understood from the ensuing detailed description of a preferred embodiment, reference being made to the accompanying drawings in which like reference characters denote like parts.

DETAILED DESCRIPTION OF PREFERRED EMBODIMENTS

Figure 1:
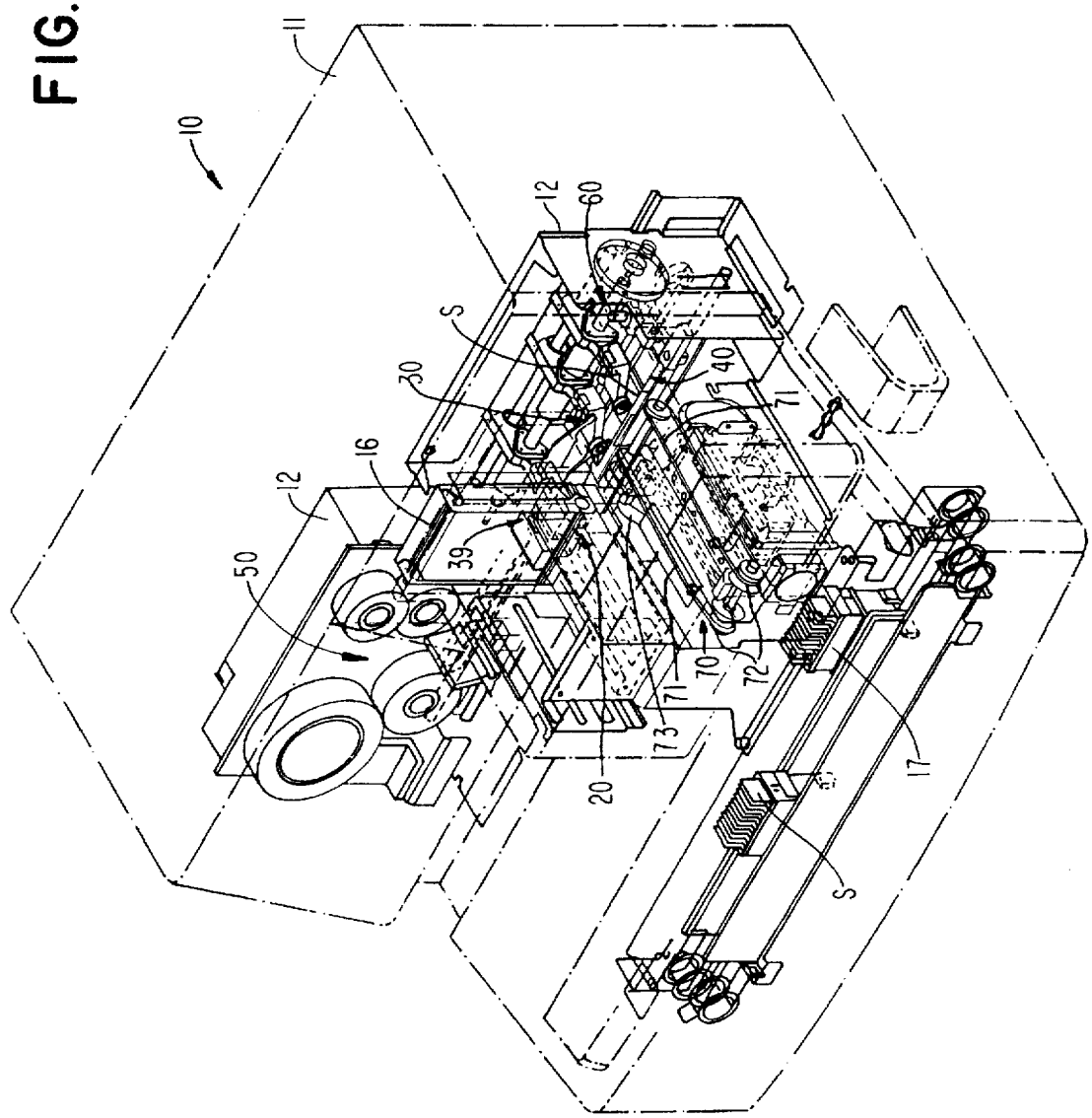
FIG. 1 is a perspective view showing portions of the interior of one automatic blood smear slide maker incorporating dryer apparatus according to the present invention.
Figure 2:
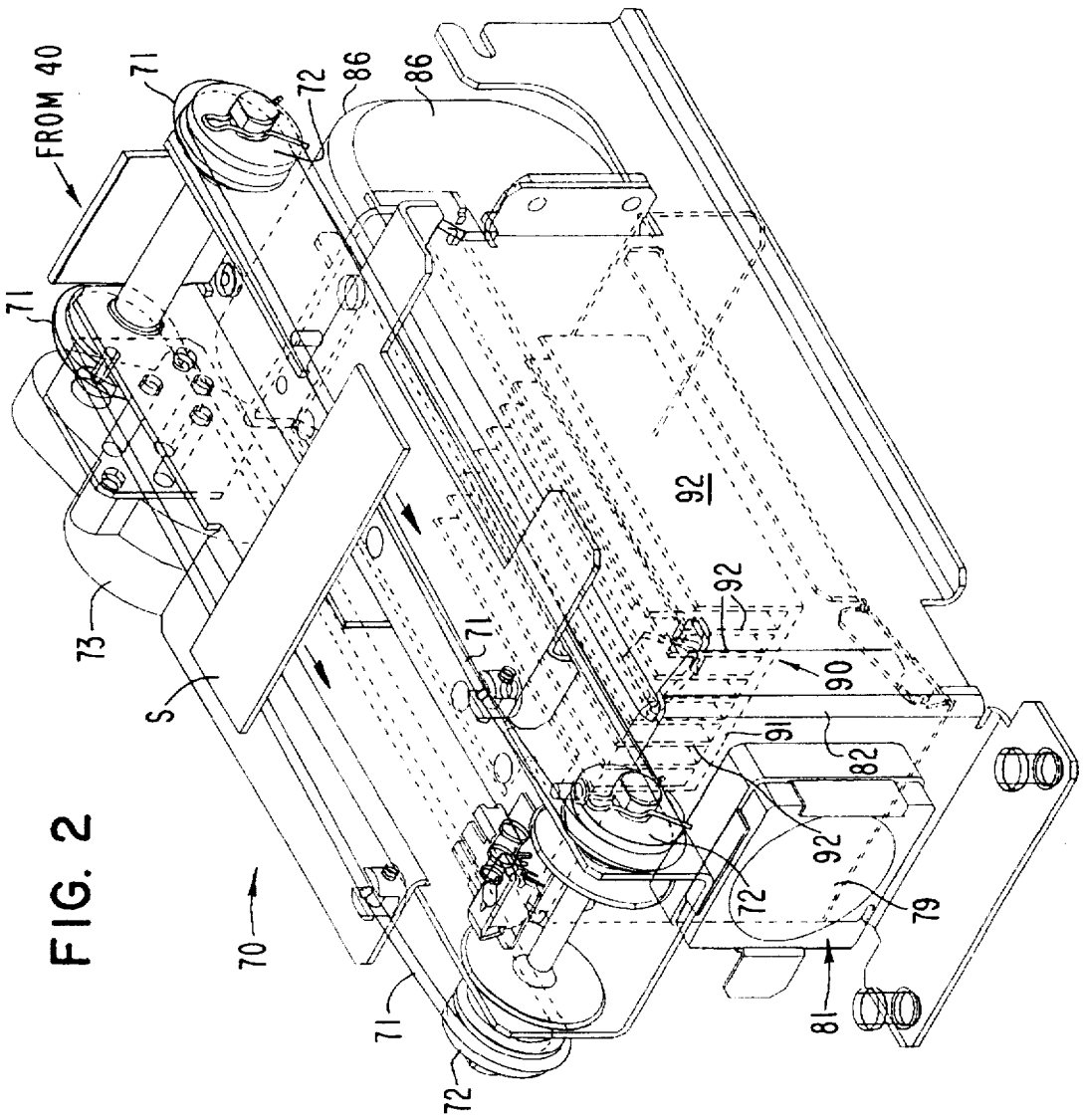
FIG. 2 is an enlarged perspective view of the dryer apparatus shown in FIG. 1.
Figure 3:
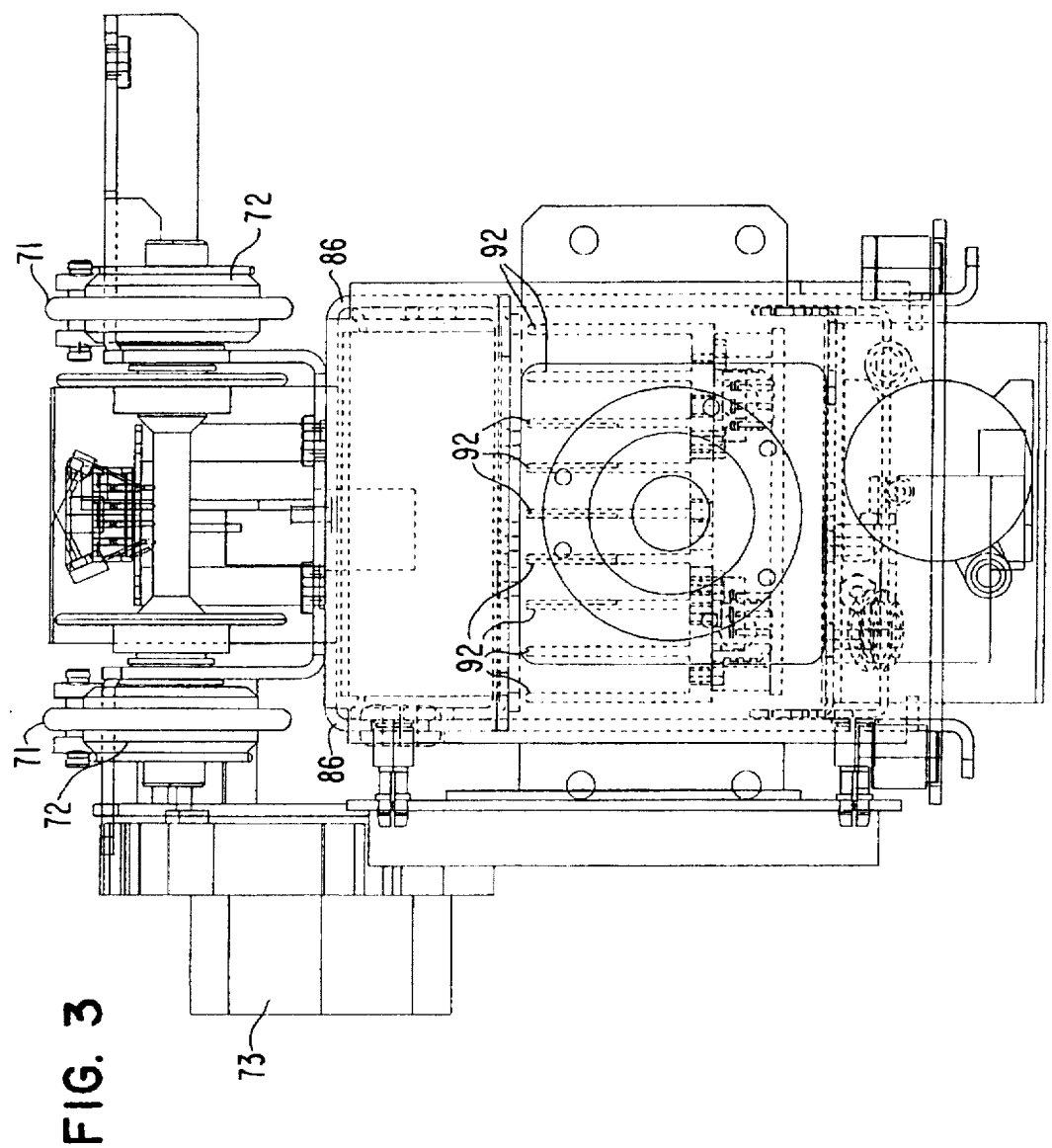
FIG. 3 is a front view of the FIG. 2 apparatus.
Figure 4:
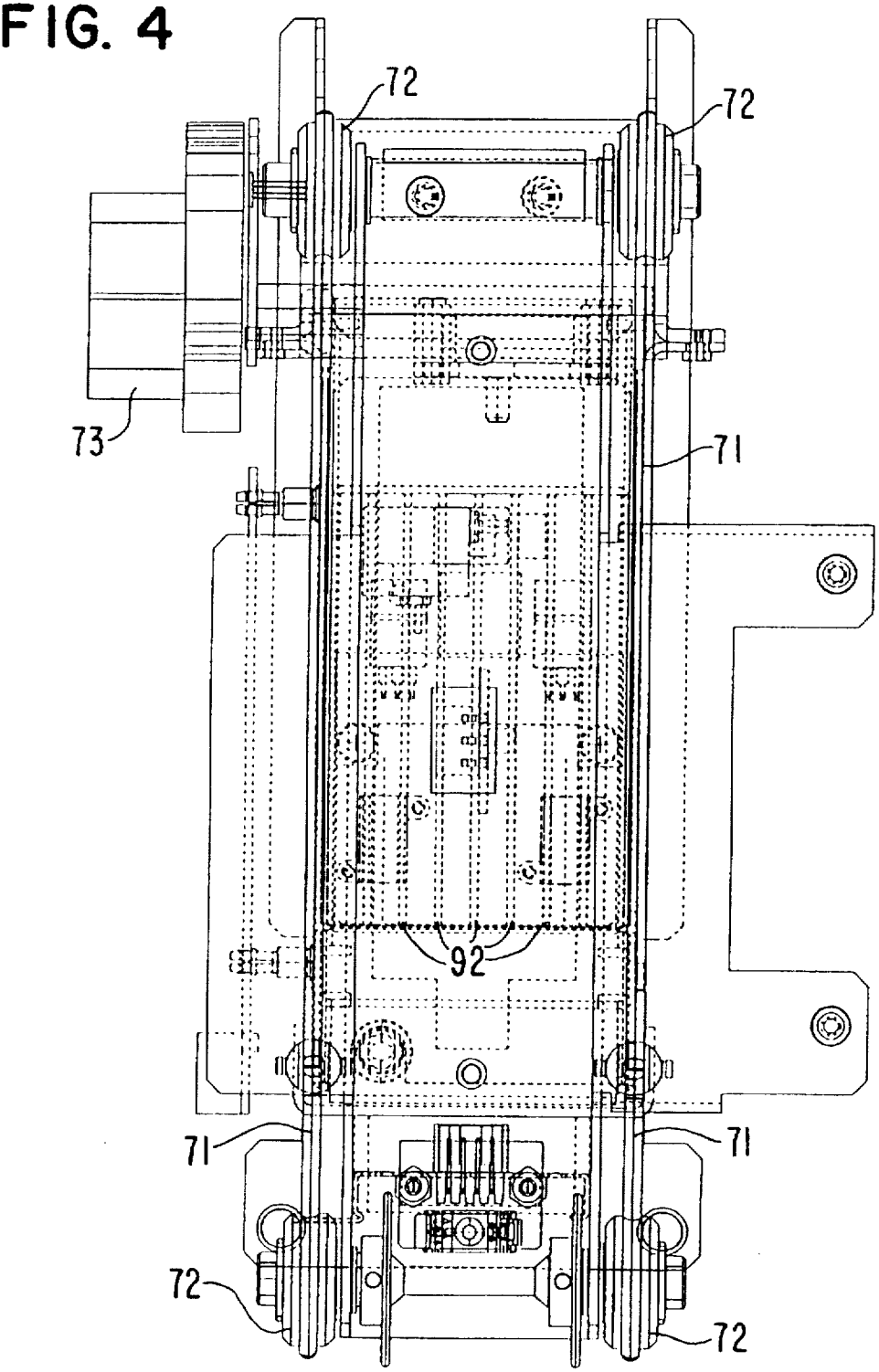
FIG. 4 is a top view of the FIG. 2 apparatus.
Figure 5:
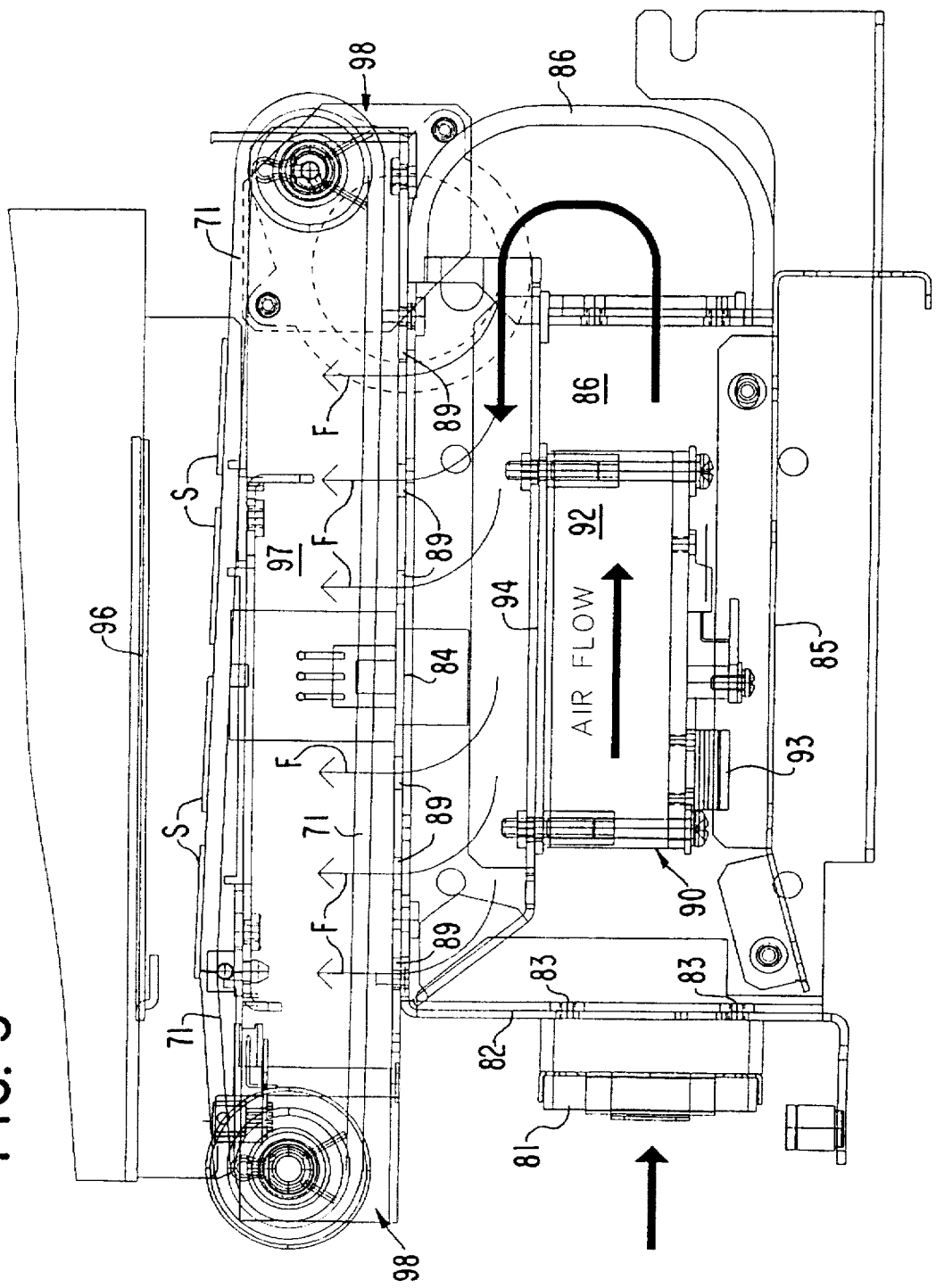
FIG. 5 is a schematic side view of the FIG. 2 dryer apparatus.

FIG. 1 illustrates an automated slidemaker 10 incorporating dryer apparatus 70 constructed according to the present invention. The automated slide maker 10 is disclosed in detail in the above-referenced U.S. application Serial No. 08/557,226, entitled "Improved Apparatus and Method for Production of Blood Smear Slides," which is incorporated herein by reference. Slide maker 10 generally comprises a number of cooperative assemblies which are located within a housing 11 and supported on a mainframe 12. Such assemblies perform different functions on specimen substrates S (e.g. 1"×3"×.04" microscope slides), received from slide cassettes 16 and outloaded into baskets 17. In general, apparatus 10 comprises a slide ejection assembly 20 for ejecting a slide from a cassette 16, a slide manipulation assembly 30 for grasping an ejected slide and using an edge thereof to smear a drop of blood on the surface of a previously ejected slide, a slide transport assembly 40 for advancing slides along a predetermined path within housing 11, a slide marking assembly 50 for imprinting specimen-identifying information on a slide, a blood drop deposition assembly 60 for depositing a drop of blood on a slide, and a slide dryer apparatus 70 for drying a blood smear on a slide. All of these assemblies operate under the control of a machine control system (e.g. a microprocessor with cooperative RAM and ROM memories and related timing control and interrupt, input and output interface sections).

As described in more detail in above noted U.S. application Ser. No. 08/557,226 an initial slide is extracted from cassette 16 and moved onto stage 39 by ejection assembly 20, where it is picked up and moved onto transport assembly 40 by manipulation assembly 30. The transport assembly 40 moves the slide S to the marking assembly 50 to where a specimen identification label L is attached to one end region. The slide is then moved (rightward as viewed in FIG. 1) to receive a blood specimen drop from assembly 60, and thence to the smear position shown in FIG. 1. During identifying and dispensing operations on the first slide, a second slide is extracted by assembly 20 and manipulated to an angular orientation (vis-a-vis the first slide) by assembly 30. The assembly 30 then moves the angularly oriented slide's edge into engagement with a blood-drop supported on a major surface of a specimen slide supported by assembly 40, and thereafter moves it leftward to produce a blood smear on the surface of the specimen slide. The specimen slide is then moved transversely off the transport assembly 40, e.g. by a solenoid operated pusher device (not shown) and into the dryer apparatus 70 of the present invention.

As shown in FIG. 1, and in more detail in FIGS. 2–5, a pair of endless cord elements 71 are mounted on pulleys 72 and driven by motor 73 to move slides from the blood smearing region, along a generally planar drying path to the outloading system of the apparatus. The cords 71 are driven slowly, e.g. about 3.5 inch/sec., in timed relation with the slide-making operations of apparatus 10, and it will be appreciated that a series of successive specimen slides will be created seriatim on the cord elements 71, with the wet blood smear surfaces facing upwardly in a common orientation that is orthogonal to the plane of their drying path.

Referring to FIGS. 2–5, the dryer apparatus 70 can be seen to further comprise an intake fan 81 which urges ambient air through an air intake control plate 82 having air inlet apertures 83. An air filter and fan guard assembly 79 is mounted on the front of fan 81 and prevents dust from passing into the dryer. Upper and lower walls 84 and 85 together with side and end walls 86 define an air plenum with an inlet end facing the control plate 82. Within the plenum air heating means 90 comprises a metal block comprising a base 91 and a plurality of upstanding fin elements 92, providing a large thermal mass, which is heated conductively by heater means 93 affixed to the lower surface of base 91. The plurality of metal-fin elements 92 provide for and extend from the heated base 91 in a configuration defining a plurality of air flow passages therebetween, from the control plate 82 to the rear end wall 86 of the plenum.

When the intake fan 81 is operated, air is drawn from the ambient atmosphere and forced through the choke apertures 83 in front wall 82 (shown in FIG. 5), along the heat transfer passages between fin elements 92, to the rear of the dryer plenum. The rear wall 86 is shaped to deflect air flows from the heat transfer passages upwardly, and then back toward the front of the plenum, over the top wall surface 94 of the heating means 90. Upper wall 84 of the air plenum overlies such return air flow and has a number of spaced air egress orifices 89 formed therein so as to provide a baffle for directing air upwardly, along flow paths substantially orthogonal to the plane of wall 84 and toward the bottom surfaces of slides S on the slide feed path extending thereover. The fan construction is selected in conjunction with the size and number of control apertures 83, and the size and number of baffle passages 89, so as to provide for a controlled air flow through the heating means and issuing from the passages of wall 84. Thus, as slides S move along the substantially planar transport path with their bottom, non-wetted surfaces generally parallel to, and equidistantly spaced from, baffle wall 84, low velocity flows F of air are directed upwardly, generally orthogonal to those lower surfaces, whereby the streams' kinetic forces are screened from blood smear specimen on the top surface of the slides S. These air flows convectively heat the glass of the slides, which, in turn, transfer heat conductively to the blood smear specimen thereon. This heating continues during the period that the slides reside above wall 84 in the dryer apparatus. A top wall 96 and side walls 97 confine the air heating region around the slide transport, but front and rear ends 98 are open for air egress. Wall 96 is spaced sufficiently above the slides path through the dryer so that no turbulent air flows occurs in contact with the blood specimen on the top surface. Thus, such convective heating of the specimen as occurs, is effected with gentle air flows.

In one preferred dryer embodiment, an intake fan having an air flow rate of 5 cubic feet per minute is used in conjunction with an air intake control plate 82 having 6 apertures of about 0.09 inch diameter. The baffle wall 84 comprises 12 spaced apertures and air flow velocity passing at those apertures is in the range of from about 40 to 100 feet per minute. This air flow velocity reduces significantly upon passing into the region surrounding the slide transport and, in typical areas adjacent slides on the transport, is in the range of about 10 to 30 feet per minute, generally toward the bottom of the slides.

In the addition to providing drying without air flow damage to the cell morphology of the blood specimens, several other features cooperate to dry the specimens without distortion. We have found that by controlling the heating air temperature to be within a predetermined range above the blood specimen temperature, (which is the same as the ambient temperature surrounding the apparatus exterior), adequate drying can be attained, along the compact drying path, without causing the blood plasma to distort the cell shapes. Thus, the dryer system comprises a temperature sensor which detects the temperature of ambient air around the slidemaker apparatus housing 10, and a temperature control servo-system is provided to energize the heater elements of the dryer 70 to maintain the heated air near the rear surface of slides at about 10° to about 20° Centigrade above the ambient temperature. Preferably the temperature is maintained about 15° C. above ambient temperatures in normal ambient ranges (e.g. 65° F. to 85° F.). One preferred system for providing such control is to detect the temperature of the heating means 90, and regulate its energization to achieve a temperature about 5° C. higher than the desired heated air temperature (e.g. to about ambient plus 20° C. to achieve heated air around the slides of ambient plus 15° C.). One useful heater element can be the power amplifier means of the heating system.

In order to maintain a proper throughput of slides, yet avoid too rapid heating, the heating path length and speed of transport cord elements 71 is selected to provide a heating period of about 75 to about 135 seconds per slide.

After passing to the end of the transport path within dryer apparatus 70, the slides are moved onto an outloader device which transfers them into baskets 17, see FIG. 1. The dryer apparatus and method of the invention has been found useful to decrease drying time (over manual ambient-drying) by about 50% in various ambient conditions (e.g. 10° C. to 45° C. and 30% to 95% relative humidity), with highly useful outputs from the viewpoint of cell morphology.

The invention has been described with reference to certain preferred embodiments but it will be appreciated that variations and modifications can be effected within the spirit and scope of the invention.

We claim:

1. In apparatus having means for automatically producing blood smears respectively on first major surfaces of a succession of glass slide elements, an improved dryer for drying each blood smear on its respective slide, said dryer comprising:
   a. means defining a plenum having an air inlet,
   b. air baffle means, defining a plenum outlet, for directing air from said plenum to different sectors of a longitudinal drying path;
   c. air flow means for inducing ambient air to flow into said plenum inlet and exit from said baffle means;
   d. means for heating air during passage through said plenum; and
   e. means for transporting slides in succession along said longitudinal drying path with their second, non-smeared, major surfaces facing the heated air flow from said baffle means, whereby the blood smears on such slides are screened from air flow stresses.

2. The invention defined in claim 1 wherein said air flow means and said air baffle means are constructed to provide air flow through said baffle means in the range of from about 40 feet per minute to about 100 feet per minute.

3. The invention defined in claim 1 further comprising temperature control means for sensing ambient air temperature and for controlling said heating means to provide air to said drying path at a temperature in the range from about 10° to about 200° Centigrade above ambient air temperature.

4. The invention defined in claim 1 wherein said transport means comprise a pair of endless feed belts located along opposite sides of said drying path to respectively support opposite end regions of the non-smeared slide surfaces.

5. The invention defined in claim 4 wherein said baffle means comprises a plate member located in generally parallel space relation to the path of said slides and having a plurality of regularly space apertures therein.

6. The invention defined in claim 5 wherein said feed path is generally horizontal.

* * * * *